(12) United States Patent
Bruno et al.

(10) Patent No.: US 7,906,280 B2
(45) Date of Patent: Mar. 15, 2011

(54) METHODS OF PRODUCING INTRACHAIN FLUOROPHORE-QUENCHER FRET-APTAMERS AND ASSAYS

(76) Inventors: John G. Bruno, San Antonio, TX (US); Joseph Chanpong, San Antonio, TX (US)

(*) Notice: Subject to any disclaimer, the term of this patent is extended or adjusted under 35 U.S.C. 154(b) by 105 days.

(21) Appl. No.: 11/433,009

(22) Filed: May 12, 2006

(65) Prior Publication Data
US 2006/0257914 A1    Nov. 16, 2006

Related U.S. Application Data

(60) Provisional application No. 60/681,084, filed on May 13, 2005.

(51) Int. Cl.
*C12Q 1/68*    (2006.01)
*G01N 33/53*    (2006.01)

(52) U.S. Cl. ......... 435/6; 435/71.2; 536/25.32; 530/409

(58) Field of Classification Search .................. None
See application file for complete search history.

(56) References Cited

U.S. PATENT DOCUMENTS

| | | | | |
|---|---|---|---|---|
| 5,866,336 A | * | 2/1999 | Nazarenko et al. | 435/6 |
| 6,399,302 B1 | * | 6/2002 | Lannigan et al. | 435/6 |
| 6,573,047 B1 | * | 6/2003 | Hung et al. | 435/6 |
| 6,680,377 B1 | * | 1/2004 | Stanton et al. | 536/22.1 |

OTHER PUBLICATIONS

Li et al. (Biochemical and Biophysical Research Communications, 2002, vol. 292, p. 31-40).*
Bock et al. (Nature, 1992, vol. 355, p. 564-566).*
Fukada et al. (Eur. J. Biochem., 2000, vol. 267, p. 3685-3694).*
Pharmalink™ Immobilization Kit 44930; 2003, p. 1-4.*
Schuette et al. (Journal of Pharmaceutical and Biomedical Analysis, 1995, vol. 13, p. 1195-1203).*
Carasquillo et al. (Investigative Opthamology & Visual Science, 2003, vol. 44, No. 1, p. 290-299).*
Hamaguchi et al. (Analytical Biochemistry, 2001, vol. 294, p. 126-131).*

* cited by examiner

*Primary Examiner* — Gary Benzion
*Assistant Examiner* — Stephanie K Mummert

(57) ABSTRACT

The present invention describes methods for the production and use of single chain (single-stranded) fluorescence resonance energy transfer ("FRET") DNA or RNA aptamers containing fluorophores (F) and quenchers (Q) at various loci within their structures, such that when its specific matching analyte is bound and the FRET-aptamers are excited by specific wavelengths of light, the fluorescence intensity of the system is modulated (increased or decreased) in proportion to the amount of analyte added. F and Q are covalently linked to nucleotide triphosphates (NTPs), which are incorporated by various nucleic acid polymerases such as Taq polymerase during the polymerase chain reaction (PCR) and then selected by affinity chromatographic, size-exclusion or molecular sieving, and fluorescence techniques. Further separation of related FRET-aptamers can be achieved by ion-pair reverse phase high performance liquid chromatography (HPLC) or other types of chromatography. Finally, FRET-aptamer structures and the specific locations of F and Q within FRET-aptamer structures are determined by digestion with exonucleases and mass spectral nucleotide sequencing analysis.

38 Claims, 7 Drawing Sheets

BoNT A DNA APTAMER SEQUENCES

BoNT A HOLOTOXIN

1 HOLOTOXIN:
CATCCGTCACACCTGCTCTGCTATCACATGCCTGCTGAAGTGGTGTTGGCTCCCGTATCA

2 HOLOTOXIN:
CATCCGTCACACCTGCTCTGCTATCACATGCCTGCTGAAGTGGTGTTGGCTCCCGTATCA

3 HOLOTOXIN:
CATCCGTCACACCTGCTCTGCTATCACATGCCTGCTGAAGTGGTGTTGGCTCCCGTATCA

4 HOLOTOXIN:
CATCCGTCACACCTGCYCYGCTATCACATGCCTGCTGAAGTGGTGTTGGCTCCCGTATCA

BoNT A 50kd ENZYMATIC SUBUNIT

1 SMALL SUBUNIT:
CATCCGTCACACCTGCTCTGGGGATGTGTGGTGTTGGCTCCCGTATCAAGGGCGAATTCT

2 SMALL SUBUNIT:
CATCCGTCACACCTGCTCTGATCAGGGAAGACGCCAACACGTGGTGTTGGCTCCCGTATCA

3 SMALL SUBUNIT:
CATCCGTCACACCTGCTCTGGGTGGGTGTTGGCTCCCGTATCAAGGGCGAATTCTGCAGATA

Fig. 4

BoNT A APTAMER COLORIMETRIC PLATE ASSAY RESULTS

Fig. 5

SNAPTIDE ASSAY BoNT A (HOLOTOXIN)

*Fig. 6A*

SNAPTIDE (50kD)

*Fig. 6B*

SEQUENCE LISTING

```
<160> NUMBER OF SEQ ID NOS: 11

<210> SEQ ID NO 1
<211> LENGTH: 60
<212> TYPE: DNA
<213> ORGANISM: Artificial Sequence
<220> FEATURE:
<223> OTHER INFORMATION: chemically synthesized

<400> SEQUENCE: 1
catccgtcac acctgctctg ctatcacatg cctgctgaag tggtgttggc tcccgtatca     60

<210> SEQ ID NO 2
<211> LENGTH: 60
<212> TYPE: DNA
<213> ORGANISM: Artificial Sequence
<220> FEATURE:
<223> OTHER INFORMATION: chemically synthesized

<400> SEQUENCE: 2
catccgtcac acctgctctg ctatcacatg cctgctgaag tggtgttggc tcccgtatca     60

<210> SEQ ID NO 3
<211> LENGTH: 60
<212> TYPE: DNA
<213> ORGANISM: Artificial Sequence
<220> FEATURE:
<223> OTHER INFORMATION: chemically synthesized

<400> SEQUENCE: 3
catccgtcac acctgctctg ctatcacatg cctgctgaag tggtgttggc tcccgtatca     60

<210> SEQ ID NO 4
<211> LENGTH: 60
<212> TYPE: DNA
<213> ORGANISM: Artificial Sequence
<220> FEATURE:
<223> OTHER INFORMATION: chemically synthesized

<400> SEQUENCE: 4
catccgtcac acctgcycyg ctatcacatg cctgctgaag tggtgttggc tcccgtatca     60

<210> SEQ ID NO 5
<211> LENGTH: 60
<212> TYPE: DNA
<213> ORGANISM: Artificial Sequence
<220> FEATURE:
<223> OTHER INFORMATION: chemically synthesized

<400> SEQUENCE: 5
```

```
catccgtcac acctgctctg gggatgtgtg gtgttggctc ccgtatcaag ggcgaattct      60
```

<210> SEQ ID NO 6
<211> LENGTH: 61
<212> TYPE: DNA
<213> ORGANISM: Artificial Sequence
<220> FEATURE:
<223> OTHER INFORMATION: chemically synthesized

<400> SEQUENCE: 6

```
catccgtcac acctgctctg atcagggaag acgccaacac gtggtgttgg ctcccgtatc      60
a                                                                     61
```

<210> SEQ ID NO 7
<211> LENGTH: 61
<212> TYPE: DNA
<213> ORGANISM: Artificial Sequence
<220> FEATURE:
<223> OTHER INFORMATION: chemically synthesized

<400> SEQUENCE: 7

```
catccgtcac acctgctctg ggtggtgttg gctcccgtat caagggcgaa ttctgcagat      60
a                                                                     61
```

<210> SEQ ID NO 8
<211> LENGTH: 60
<212> TYPE: DNA
<213> ORGANISM: Artificial Sequence
<220> FEATURE:
<223> OTHER INFORMATION: chemically synthesized

<400> SEQUENCE: 8

```
catccgtcac acctcctctg ctatcagatg cctggtgaag tggtgttggc tcccgtatca      60
```

<210> SEQ ID NO 9
<211> LENGTH: 61
<212> TYPE: DNA
<213> ORGANISM: Artificial Sequence
<220> FEATURE:
<223> OTHER INFORMATION: chemically synthesized

<400> SEQUENCE: 9

```
catccgtcac acctgctctg atcagggaag acgccaacac gtggtgttgg ctcccgtatc      60
a                                                                     61
```

<210> SEQ ID NO 10
<211> LENGTH: 60
<212> TYPE: DNA
<213> ORGANISM: Artificial Sequence
<220> FEATURE:
<223> OTHER INFORMATION: chemically synthesized

<400> SEQUENCE: 10

```
catccgtcac acctgctctg gggatgtgtg gtgttggctc cggtatcaag ggcgaattct      60
```

<210> SEQ ID NO 11
<211> LENGTH: 61
<212> TYPE: DNA
<213> ORGANISM: Artificial Sequence -continued

```
<220> FEATURE:
<223> OTHER INFORMATION: chemically synthesized

<400> SEQUENCE: 11
catccgtcac acctcctctg ggtggtgttg ggtccggtat caagggccaa ttctgcagat    60
a                                                                    61
```

METHODS OF PRODUCING INTRACHAIN FLUOROPHORE-QUENCHER FRET-APTAMERS AND ASSAYS

This application is based upon and claims priority from U.S. Provisional application Ser. No. 60/681,084, filed May 13, 2005 which is incorporated herein by reference.

BACKGROUND OF THE INVENTION

1. Field of the Invention

Applicants' invention relates to the field of aptamer- and nucleic acid-based diagnostics. More particularly, it relates to methods for the production and use of single chain (single-stranded) fluorescence resonance energy transfer ("FRET") DNA or RNA aptamers containing fluorophores ("F") and quenchers ("Q") at various loci within their structures.

2. Background Information

FRET-aptamers are a new class of compounds desirable for their use in rapid (within minutes), one-step, homogeneous assays involving no wash steps (simple bind and detect quantitative assays). Several individuals and groups have published and patented FRET-aptamer methods for various target analytes that consist of placing the F and Q moieties either on the 5' and 3' ends respectively to act like a "molecular (aptamer) beacon" or placing only F in the heart of the aptamer structure to be "quenched" by another proximal F or the DNA or RNA itself. These preceding FRET-aptamer methods are all highly engineered and based on some prior knowledge of particular aptamer sequences and secondary structures, thereby enabling clues as to where F might be placed in order to optimize FRET results.

Until now, no individual or group has described a method for natural selection of single chain (intrachain) FRET-aptamers that contain both fluorophore-labeled deoxynucleotides ("F-dNTPs") and highly efficient spectrally matched quencher ("Q-dNTP") moieties in the heart of an aptamer binding loop or pocket by polymerase chain reaction ("PCR"). The advantage of this F and Q "doping" method is two-fold: 1) the method allows nature to take its course and select the most sensitive FRET-aptamer target interactions in solution, and 2) the positions of F and Q within the aptamer structure can be determined via exonuclease digestion of the FRET-aptamer followed by mass spectral analysis of the resulting fragments, thereby eliminating the need to "engineer" the F and Q moieties into a prospective aptamer binding pocket or loop. Sequence and mass spectral data can be used to further optimize the FRET-aptamer assay performance after natural selection as well.

Others have described nucleic acid-based "molecular beacons" that snap open upon binding to an analyte or upon hybridizing to a complementary sequence, but beacons are always end-labeled with F and Q at the 3' and 5' ends. FRET-aptamers may be labeled anywhere in their structure that places the F and Q within the Forster distance of approximately 60-85 Angstroms to achieve quenching prior to or after target analyte binding to the aptamer "binding pocket" (typically a "loop" in the secondary structure).

"Signaling aptamers" do not include a Q in their structures, but rather appear to rely upon the "self-quenching" of two adjacent fluorophores or the mild quenching ability of the nucleic acid itself. Both of these methods of quenching are relatively poor, because eventually F-emitted photons escape into the environment and are detectable, thereby contributing to background light and limiting the sensitivity of the FRET assay. True quenchers such as dabcyl ("D"), the "Black Hole Quenchers" ("BHQs"), and the QSY family of dyes (QSY-5, QSY-7, or QSY-9) are broad spectrum absorbing molecules that appear dark or even black in color, because they absorb many wavelengths of light and do not re-emit photons. The inclusion of a Q in the intrachain FRET-aptamer structure or the competitive aptamer FRET format, reduces background fluorescence intensity significantly, thereby increasing signal-to-noise ratios and improving assay sensitivity.

In addition to the novelty of the quencher introduction into the assay formats and advantages conferred in terms of sensitivity by cutting background fluorescence, the method of selecting single intrachain FRET-aptamers based on differential molecular weight and fluorescence intensity of the target analyte-aptamer bound subset fractions is a novel FRET-aptamer development method. The F and Q molecules used can include any number of appropriate fluorophores and quenchers as long as they are spectrally matched so the emission spectrum of F overlaps significantly (almost completely) with the absorption spectrum of Q.

SUMMARY OF THE INVENTION

The present invention describes a single chain (single-stranded intrachain) FRET assay approach in which F and Q are incorporated into an aptamer population via their nucleotide triphosphate derivatives (for example, ALEXFLUOR™-NTPs, CASCADE BLUE®-NTPs, CHROMATIDE®-NTPs, fluorescein-NTPs, rhodamine-NTPs, RHODAMINE GREEN™-NTPs, tetramethylrhodamine-dNTPs, OREGON GREEN®-NTPs, and TEXAS RED®-NTPs may be used to provide the fluorophores, while dabcyl-NTPs, Black Hole Quencher or BHQ™-NTPs, and QSY™ dye-NTPs may be used for the quenchers) by PCR after several rounds of selection and amplification without the F- and Q-modified bases. This process is generally referred to as "doping" with F-NTPs and Q-NTPs.

Thereafter, the single chain or intrachain FRET-aptamers in the population that still bind the intended target (after the doping process) are purified by size-exclusion chromatography columns, spin columns, gel electrophoresis or other means. Once bound and separated based on weight or other physical properties, the brightest fluorescing FRET-aptamer-target complexes are selected because they are clearly the optimal FRET candidates. The FRET-aptamers are separated from the targets by heating or chemical means (urea, etc.) and purified again by size-exclusion chromatography or other means.

These intrachain FRET-aptamers cannot be cloned for sequencing due to the need for determining the locations of F and Q in their structures. Cloning would lead to replication of the FRET-aptamer insert in the plasmid and either dilution of the desired FRET-aptamer or alteration of its F and Q locations within the aptamer. Therefore, the candidate FRET-aptamers are separated based on physical properties such as charge or weak interactions by various types of high performance liquid chromatography ("HPLC"), digested at each end with specific exonucleases (snake venom phosphodiesterase on the 3' end and calf spleen phosphodiesterase on the 5' end). The resulting oligonucleotide fragments, each one base shorter than the predecessor, are subjected to mass spectral analysis which can reveal the nucleotide sequences as well as the positions of F and Q within the FRET-aptamers. Once the FRET-aptamer sequence is known with the positions of F and Q, it can be further manipulated during solid-phase DNA or RNA synthesis in an attempt to make the FRET assay more sensitive and specific.

There are a number of uses of the single-chain FRET-aptamers developed by the present invention, including quantifiable fluorescence assays for small molecules including pesticides, natural and synthetic amino acids and their derivatives (e.g., histidine, histamine, homocysteine, DOPA, melatonin, nitrotyrosine, etc.), short chain proteolysis products such as cadaverine, putrescine, the polyamines spermine and spermidine, nitrogen bases of DNA or RNA, nucleosides, nucleotides, and their cyclical isoforms (e.g., cAMP and cGMP), cellular metabolites (e.g., urea, uric acid), pharmaceuticals (therapeutic drugs), drugs of abuse (e.g., narcotics, hallucinogens, gamma-hydroxybutyrate, etc.), cellular mediators (e.g., cytokines, chemokines, immune modulators, neural modulators, inflammatory modulators such as prostaglandins, etc.), or their metabolites, explosives (e.g., trinitrotoluene) and their breakdown products or byproducts, peptides and their derivatives. Other uses of the single-chain FRET-aptamers include use in quantifiable fluorescence assays for macromolecules including proteins such as biotoxins including botulinum toxins, Shiga toxins (See FIG. 2), staphylococcal enterotoxins, other bacterial toxins, prions such as bovine spongiform encephalopathies ("BSEs") and transmissible spongiform encephalopathies ("TSEs"), glycoproteins, lipids, glycolipids, triglycerides, nucleic acids, polysaccharides, lipopolysaccharides, etc. The single-chain FRET-aptamers may also be used in quantifiable fluorescence assays for subcellular and whole cell targets including subcellular organelles such as ribosomes, Golgi apparatus, vesicles, microfilaments, microtubules, etc., viruses, virions, rickettsiae, bacteria, protozoa, plankton, parasites such as *Cryptosporidium* species, *Giardia* species, mammalian cells such as various classes of leukocytes, neurons, stem cells, cancer cells, etc.

The use of unlabeled aptamer sequence information and secondary stem-loop structures may aid in the determination and engineered optimization of F or Q placement within the aptamer structure to maximize FRET assay sensitivity and specificity. Although, an anticipated step in the present method of natural selection of F- and/or Q-labeled aptamers to form solution phase interactions with their target analytes, additional sequence and secondary structure information can be used to confirm and enhance F and Q placement to optimize assay performance.

BRIEF DESCRIPTION OF THE DRAWINGS

FIG. 4. illustrates sample aptamer sequences.

FIG. 5. is a line graph correlating absorbance with BoNT A concentration.

FIGS. 6A-6B. are line graphs mapping fluorescence intensity against time.

DETAILED DESCRIPTION OF THE PREFERRED EMBODIMENT

Figure 1:
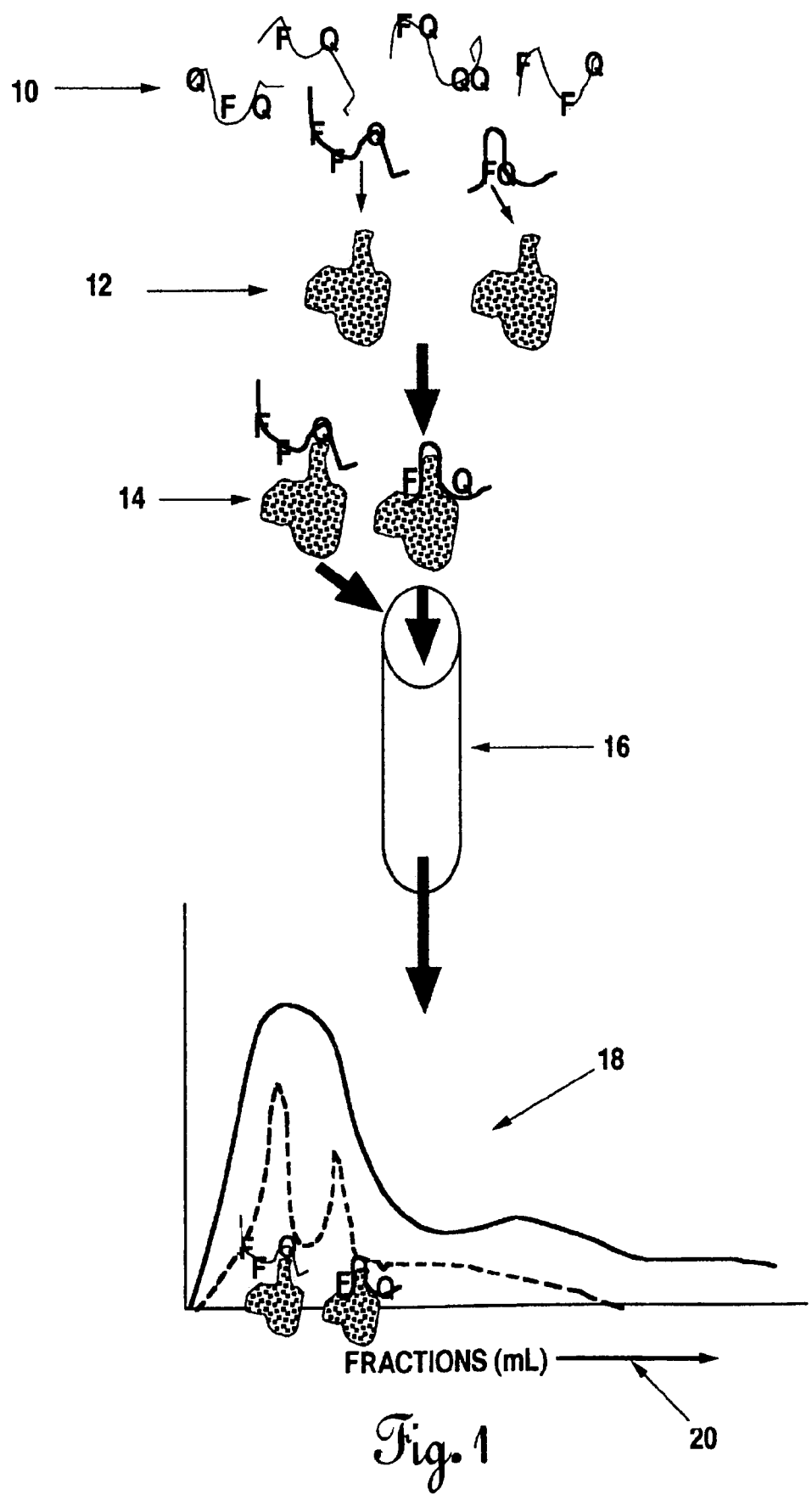
FIG. 1. is a schematic illustration of the single chain (intrachain) FRET-aptamer selection method.

Referring to the figures, FIG. 1. illustrates a single chain (intrachain) FRET-aptamer selection method. This method consists of several steps. First the random DNA library of oligonucleotides (randomized region of 20 or more bases flanked by known primer regions) is "doped" with F-dNTPs Q-dNTPs by the PCR (10). The F and Q doped library is then exposed to a protein or other target molecule (12). Some members of the doped library will bind to the target protein (14).

If the target molecule is a larger water-soluble molecule such as a protein, glycoprotein, or other water soluble macromolecule, then exposure of the nascent F-labeled and Q-labeled DNA or RNA random library to the free target analyte is done in solution. If the target is a soluble protein or other larger water-soluble molecule, then the optimal FRET-aptamer-target complexes are separated by size-exclusion chromatography. The FRET-aptamer-target complex population of molecules is the heaviest subset in solution and will emerge from a size-exclusion column first, followed by unbound FRET-aptamers and unbound proteins or other targets. Among the subset of analyte-bound aptamers there will be heterogeneity in the numbers of F-and Q-NTPs that are incorporated as well as nucleotide sequence differences, which will again effect the mass, electrical charge, and weak interaction capabilities (e.g., hydrophobicity and hydrophilicity) of each analyte-aptamer complex. These differences in physical properties of the aptamer-analyte complexes can then be used to separate out or partition the bound from unbound analyte-aptamer complexes.

If the target is a small molecule (generally defined as a molecule with molecular weight of $\leq 1,000$ Daltons), then exposure of the nascent F-labeled and Q-labeled DNA or RNA random library to the target is done by immobilizing the target. The small molecule can be immobilized on a column, membrane, plastic or glass bead, magnetic bead, or other matrix.

If no functional group is available on the small molecule for immobilization, the target can be immobilized by the Mannich reaction (formaldehyde-based condensation reaction) on a device similar to a PHARMALINK™ column. Elution of bound DNA from the small molecule affinity column, membrane, beads or other matrix by use of 0.2-3.0M sodium acetate at a pH ranging between 3 and 7, although the optimal pH is approximately 5.2.

These can be separated from the non-binding doped DNA molecules by running the aptamer-protein aggregates (or selected aptamers-protein aggregates) through a size-exclusion column, by means of size-exclusion chromatography using Sephadex™ or other gel materials in the column (16). Since they vary in weight due to variations in aptamers sequences and degree of labeling, they can be separated into fractions with different fluorescence intensities. Purification methods such as preparative gel electrophoresis are possible as well. Small volume fractions ($\leq 1$ mL) can be collected from the column and analyzed for absorbance at 260 nm and 280 nm which are characteristic wavelengths for DNA and proteins. The heaviest materials come through a size-exclusion column first. Therefore, the DNA-protein complexes will come out of the column before either the DNA or protein alone.

Means of separating FRET-aptamer-target complexes from solution by alternate techniques (other than size-exclusion chromatography) include, without limitation, molecular weight cut off spin columns, dialysis, gel electrophoresis, thin layer chromatography (TLC), and differential centrifugation using density gradient materials.

The optimal (most sensitive or highest signal to noise ratio) FRET-aptamers among the bound class of FRET-aptamer-target complexes are identified by assessment of fluorescence intensity for various fractions of the FRET-aptamer-target class. The separated DNA-protein complexes will exhibit the highest absorbance at established wavelengths, such as 260 nm and 280 nm similar to that graphed in FIG. 1 (18). The fractions showing the highest absorbance at the given wavelengths, such as 260 nm and 280 nm, are then further analyzed for fluorescence and those fractions exhibiting the greatest fluorescence are selected for separation and sequencing (20).

These similar FRET-aptamers may be further separated using techniques such as ion pair reverse-phase HPLC, ion-exchange chromatography ("IEC", either low pressure or HPLC versions of IEC), thin layer chromatography (TLC), capillary electrophoresis, or similar techniques.

The final FRET-aptamers are able to act as one-step "lights on" or "lights off" binding and detection components in assays.

Intrachain FRET-aptamers that are to be used in assays with long shelf-lives may be lyophilized (freeze dried) and reconstituted.

Figure 2:
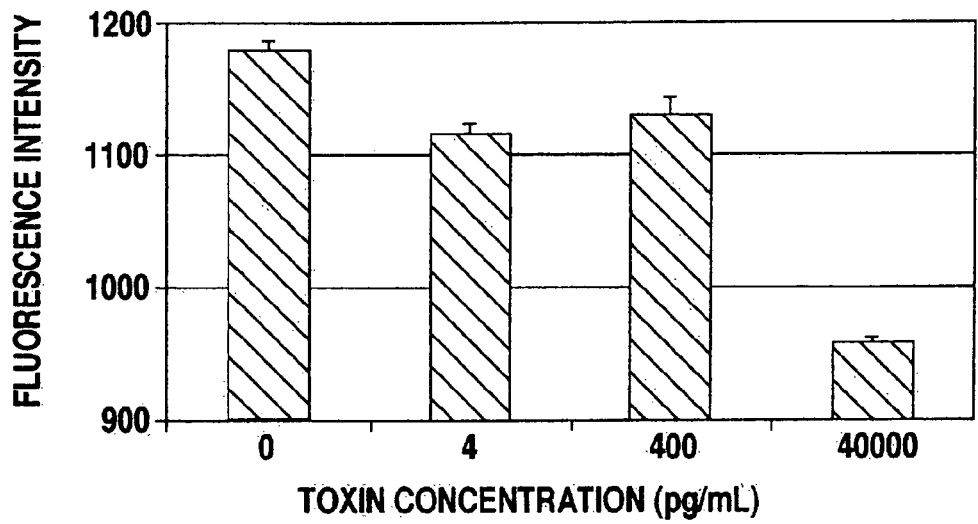
FIG. 2. is a bar graph showing toxin concentration mapped with fluorescence intensity and illustrating a "lights off" FRET with shiga-like toxin 1 and round 5 aptamers.

FIG. 2. is a bar graph showing toxin concentration mapped with fluorescence intensity and illustrating a "lights off" FRET with shiga-like toxin 1 and round 5 aptamers. If the fluorescence intensity of the DNA aptamers is correlated to the concentration of the surface protein and the fluorescence intensity decreases as a function of increasing analyte concentration, then it is referred to as a "lights off" assay. If the fluorescence intensity increases as a function of increasing analyte concentration, then it is referred to as a "lights on" assay. Intrachain FRET-aptamer assay data for detection of *E. coli* shiga-like toxin 1 protein resulting in a "lights off" FRET reaction as a function of toxin concentration. Fluorescence readings were obtained within five minutes of toxin addition.

Figure 3:
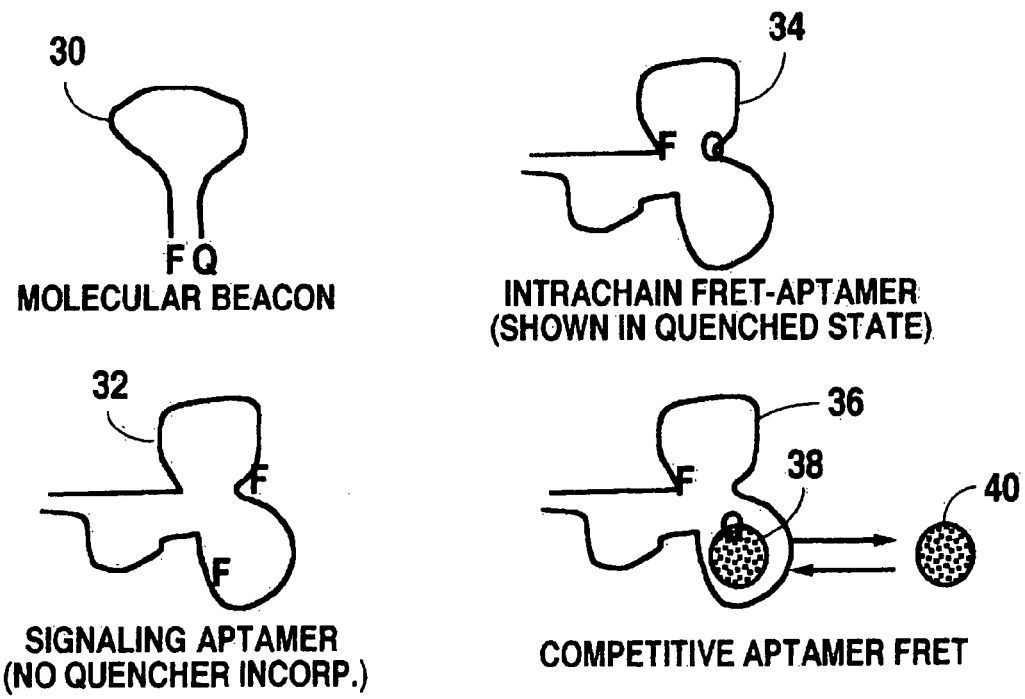
FIG. 3. is a schematic illustration that illustrates a comparison of possible nucleic acid FRET assay formats.

FIG. 3. illustrates a comparison of possible nucleic acid FRET assay formats. Upper left is a molecular beacon (30) which may or may not be an aptamer, but is typically a short oligonucleotide used to hybridize to other DNA or RNA molecules and exhibit FRET upon hybridizing. Molecular beacons are only labeled with F and Q at the ends of the DNA molecule. Lower left is a signaling aptamer (32), which does not contain a quencher molecule, but relies upon fluorophore self-quenching or weak intrinsic quenching of the DNA or RNA to achieve limited FRET. Upper right is an intrachain FRET-aptamer (34) containing F and Q molecules built into the interior structure of the aptamer. Intrachain FRET-aptamers are naturally selected and characterized by the processes described herein. Lower right shows a competitive aptamer FRET (36) motif in which the aptamer contains either F or Q and the target molecule (38) is labeled with the complementary F or Q. Introduction of unlabeled target molecules (40) then shifts the equilibrium so that some labeled target molecules (38) are liberated from the labeled aptamer (36) and modulate the fluorescence level of the solution up or down thereby achieving FRET. A target analyte (40) is either unlabeled or labeled with a quencher (Q). F and Q can be switched from placement in the aptamer (36) to placement in the target analyte (40) and vice versa.

FIG. 4 illustrates sample aptamer sequences in which all sequences are arranged 5' to 3' from left to right. The actual degenerate (randomized) aptamer regions are bolded. Clear consensus regions are bolded and italicized. Flanking sequences match with the primers used in the PCR scheme or the complementary strand primer sequences except in highlighted cases. Most sequences end in a 3' A (added by Taq, underlined). Aptamer sequences that bind and inhibit the action of botulinum A (BONT A) 150 kD holotoxin and the 50 kD enzymatic subunit of BoNT A, and which may be useful in single chain FRET-aptamer or competitive aptamer-FRET assays for detection and quantization of BoNT A.

Figure 4A:
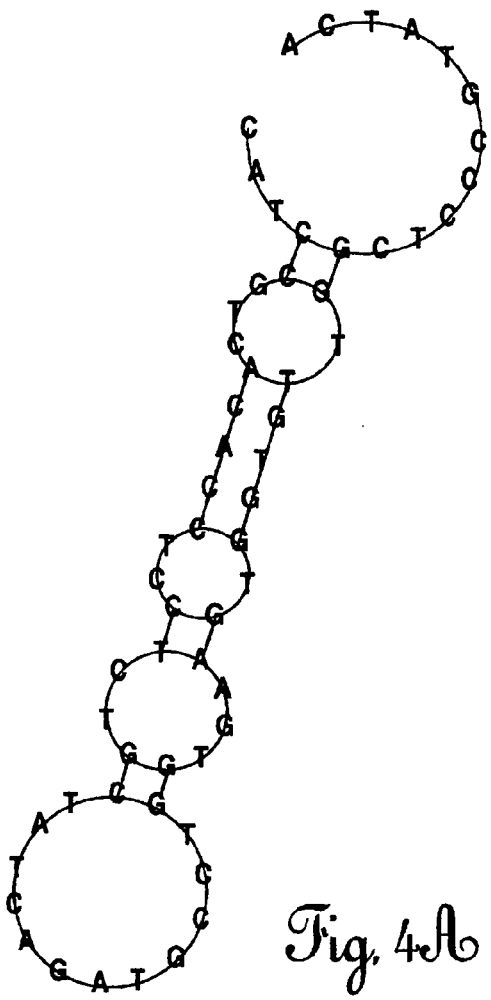
FIGS. 4A-4D. are schematic illustrations of the structures of selected aptamer sequences shown in FIG. 4.
Figure 4B:
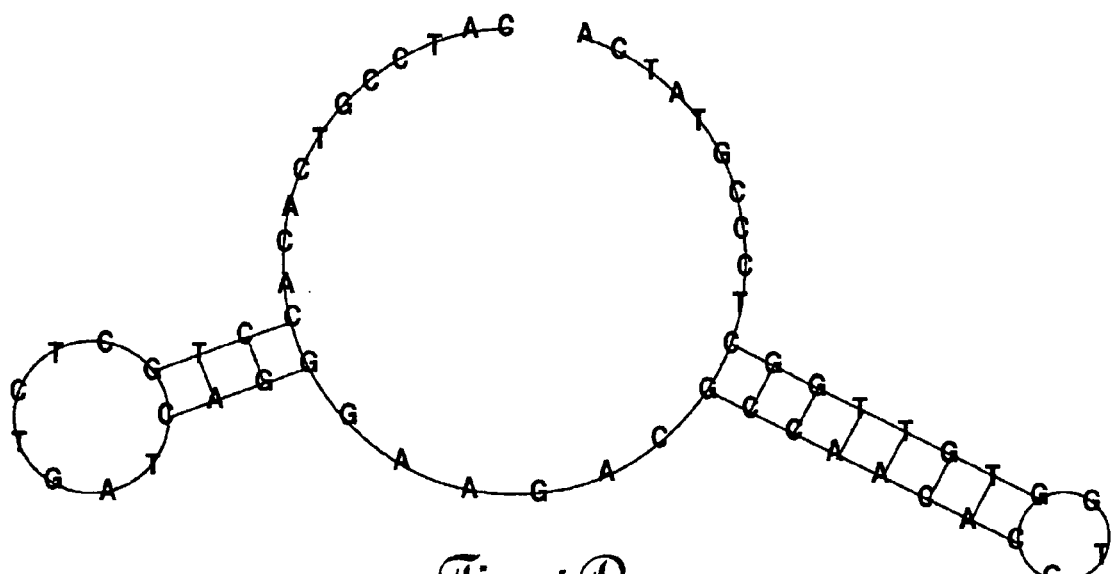
Figure 4C:
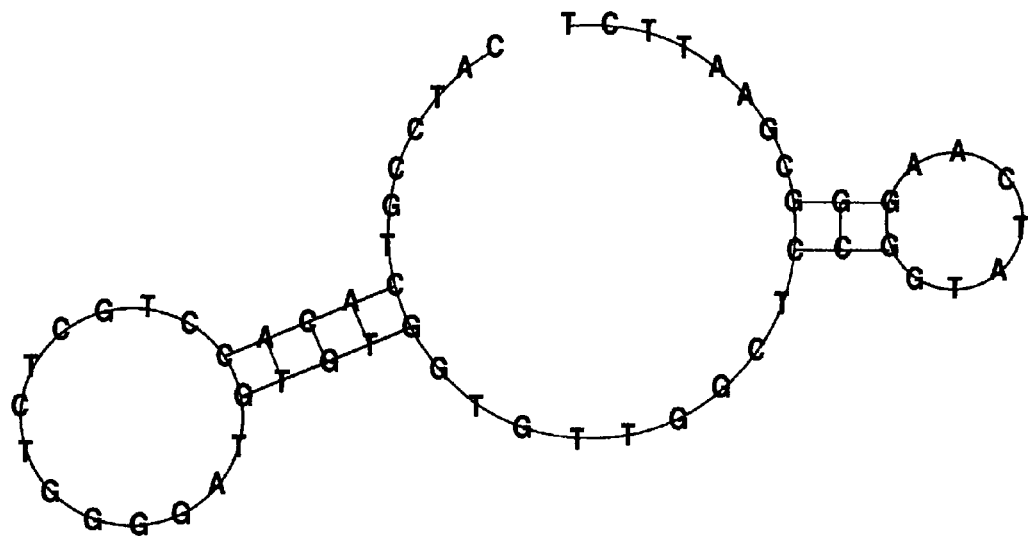
Figure 4D:
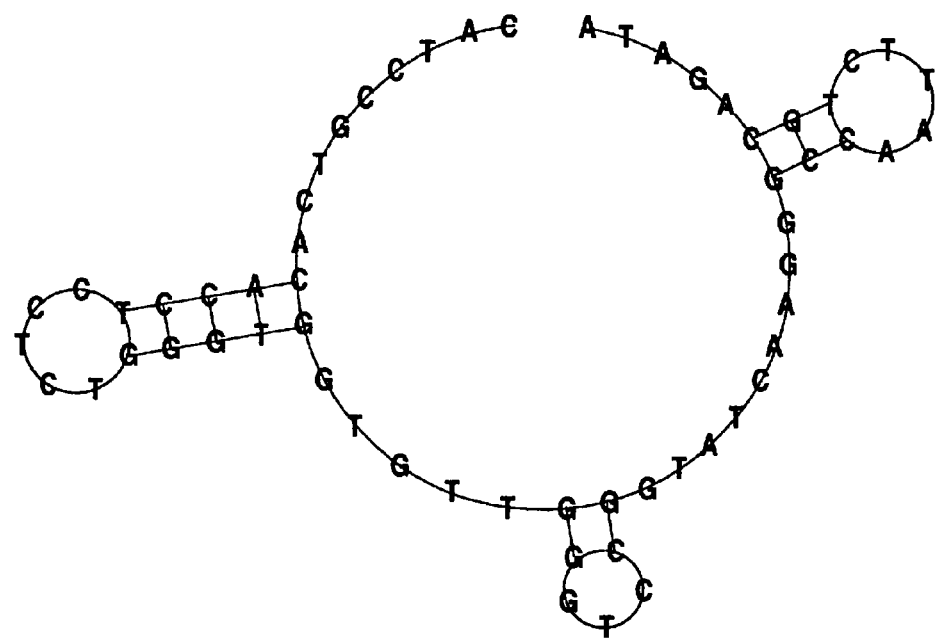

FIGS. 4A-4D. illustrate structures of selected aptamer sequences listed in FIG. 4. Various botulinum A (BONT A) DNA aptamer secondary stem-loop structures that bind the holotoxin (FIG. 4A, which exemplifies a sequence that occurred in four different clones), and bind and inhibit (See FIGS. 6A and 6B) the small (50 kD) enzymatic subunit (FIGS. 4B-4D, showing the secondary structures for three different sequences that produced similar secondary structures).

Figure 5:
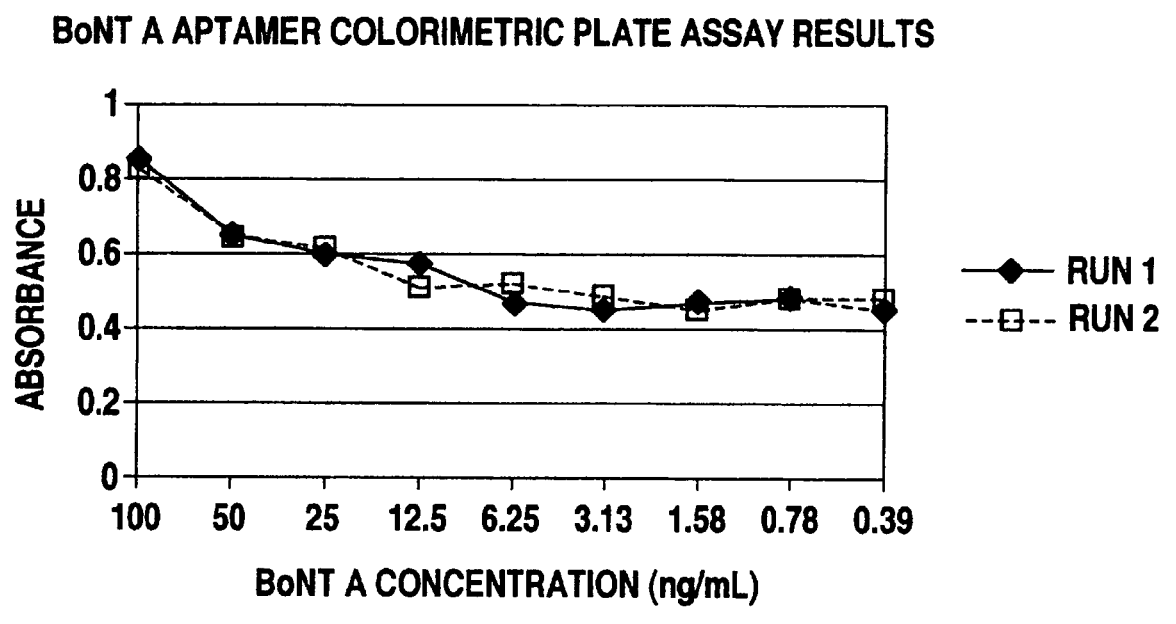

FIG. 5. is a line graph correlating absorbance with BoNT A concentration. It illustrates that aptamer-peroxidase calorimetric plate binding assay results using polyclonal BoNT A aptamers and BoNT A holotoxin. Two different trials or runs are shown. Absorbance was quantified at 405 nm using standard ABTS substrate reagents. The curves illustrate binding and sensitive detection of BoNT A by the aptamers at a level of at least 12.5 ng/mL.

Figures 6A, 6B:
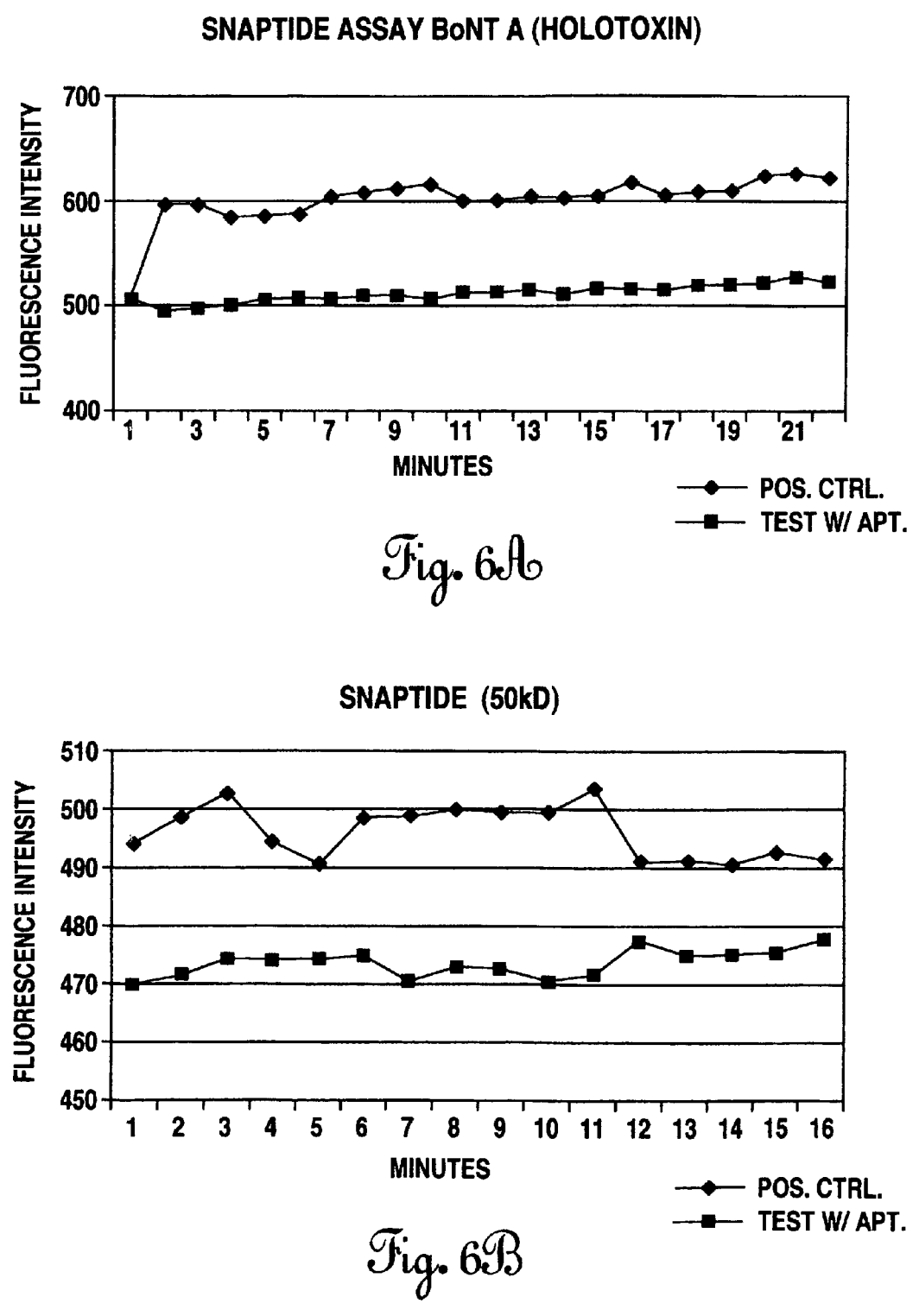

FIGS. 6A-6B. are line graphs mapping the fluorescence intensity of the DNA aptamers such as those shown in FIGS. 4A-4D against time in minutes. DNA aptamers, such as those shown in FIGS. 4A-4D, bind and inhibit the enzymatic activity of BoNT A. FIG. 6A shows assay results using the BoNT A holotoxin and FIG. 6B shows results using the isolated 50 kd enzymatic subunit of BoNT A.

The positive control line shows greater fluorescence intensity over time for the uninhibited SNAPTIDE™ assay and the "Test with Aptamer" line shows consistent suppression of the fluorescence intensity of the SNAPTIDE™ assay proving aptamer-mediated inhibition of BoNT A enzymatic activity.

EXAMPLE 1

Single (Intrachain) Chain FRET-Aptamer Assay for a Protein (*E. coli* Shiga-Like Toxin I).

Following five rounds of systematic evolution of ligands by exponential enrichment ("SELEX") an aptamer family was subjected to PCR in the presence of 3 μM CHROMATIDE™-dUTP and 40 μM Dabcyl-dUTP using a standard PCR mix formulation and Taq enzyme at 1 Unit per 50 μL reaction. This led to incorporation of the FRET (F and Q) pair which demonstrated the lowest background fluorescence of all F:Q ratios tested (nearly 1,200 fluorescence units for the baseline reading without the toxin target). Fluorescence readings in FIG. 2 were taken with a handheld fluorometer. Error bars in FIG. 2 represent the standard deviation of three trials and the bar heights represent the means of the 3 measurements. At the level of 40,000 picograms per milliliter (pg/mL) or 40 nanograms (ng) of Shiga-like toxin I, a definitive "lights off" FRET effect is noted. Since the mean fluorescence at 40 ng of added toxin is far greater than two standard deviations below any of the other treatment groups, it must be considered statistically significant.

EXAMPLE 2

Use of Unlabeled Aptamer Nucleotide Sequences and Secondary (Stem-Loop) Structures that Can Confirm, Enhance, and Optimize FRET-aptamer Assays.

The present method enables the natural selection of FRET-aptamers. However, the method can be confirmed and enhanced by knowledge of the unlabeled aptamer sequences and structures that were selected from several rounds of SELEX before the aptamer population was "doped" with F-dNTPs and/or Q-dNTPs. FIG. 4 gives an example of BoNT A aptamer sequences that are claimed as unlabeled sequences, resulting in secondary stem-loop structures from energy minimization software using 25° C. as the nominal binding temperature. The stem-loop structures shown in FIGS. 4A-4D may be especially useful in determining if the F and Q locations are indeed logical (i.e., fall in or near a binding loop structure). In addition, if F and/or Q loci are found to be distal, information such as the secondary structures in FIGS. 4A-4D could be instrumental in slightly relocating the F and Q moieties to enhance or optimize the FRET assay results in terms of assay sensitivity and specificity.

Aptamers were incorporated into plasmids. The plasmids were purified and sequenced by capillary electrophoresis following PCR.

The BoNT A functionality of the aptamer sequences (ability to bind and inhibit BoNT A) shown in FIGS. 4 and 4A-4D were confirmed by colorimetric plate assay binding data (FIG. 5) and SNAPTIDE™ FRET assay data showing inhibition of BoNT A enzymatic activity by the "polyclonal" family of BoNT A aptamers (FIG. 6).

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

What is claimed:

1. A method of generating single-chain fluorescence resonance energy transfer ("FRET")-aptamers that contain both fluorophores and quenchers in the same single-stranded oligonucleotides, comprising:
   incorporating fluorophores and quenchers into an aptamer population using polymerase chain reaction ("PCR") wherein at least one of said fluorophores and at least one of said quenchers are incorporated into some of said oligonucleotides at random locations in the interior of said oligonucleotides;
   exposing said aptamer population to a population of target molecules; and
   separating, in a first separating step, those FRET-aptamers that have bound to a target molecule and which emit minimal detectable fluorescence prior to binding said target molecule but emit increased detectable fluorescence after binding said target molecule, from the remaining aptamer population.

2. The method of claim 1, further comprising selecting a best FRET-aptamer that exhibits the brightest fluorescence from said FRET-aptamers.

3. The method of claim 1, wherein said target molecules are proteins.

4. The method of claim 1, wherein said first separating step is accomplished via one of size-exclusion chromatography columns, spin columns, or gel electrophoresis.

5. The method of claim 2, further comprising determining the nucleotide sequence of said best FRET-aptamer.

6. The method of claim 2, further comprising separating, in a second separating step, said FRET-aptamers that have bound to a target molecule from said target molecule wherein said second separating step is accomplished via introduced heating or chemicals.

7. The method of claim 6, further comprising separating, in a third separating step, said FRET-aptamers based upon specific physical properties.

8. The method of claim 1, wherein said fluorophores are selected from the group consisting of sulfonated versions of coumarins, rhodamine, xanthene dyes like fluoresceins and cyanine dyes such as ALEXFLUOR™-NTPs, pyreneoxytrisulfonic acid such as CASCADE BLUE®-NTPs, fluorescent dyes such as CHROMATIDE®-NTPs, fluorescein-NTPs, rhodamine-NTPs, carboxyrhodamines such as RHODAMINE GREEN™-NTPs, tetramethylrhodamine-dNTPs, fluorinated versions of fluorescein such as OREGON GREEN®-NTPs, and sulforhodamines such as TEXAS RED®-NTPs.

9. The method of claim 1, wherein said quenchers are selected from the group consisting of dabcyl-NTPs, nonfluorescent aromatic heterocycles such as BLACK HOLE QUENCHER or BHQ™-NTPs, and diarylrhodamine or nitrobenzoxazole quencher dyes such as QSY™ dye-NTPs.

10. The method of claim 1, wherein if said target molecule is a small molecule, wherein a small molecule is defined as a molecule with a molecular weight of ≦1,000 Daltons, then said exposing step is accomplished by immobilizing said small target molecule.

11. The method of claim 10, wherein said immobilizing step is accomplished on a column, membrane, plastic or glass bead, magnetic bead, or other matrix.

12. The method of claim 11, further comprising eluting bound aptamers from said column, membrane, plastic or glass bead, magnetic bead, or other matrix by use of 0.2-3.0M sodium acetate at a pH of between 3 and 7.

13. The method of claim 11, further comprising eluting bound aptamers from said column, membrane, plastic or glass bead, magnetic bead, or other matrix by use of 0.2-3.0M sodium acetate at a pH of 5.2.

14. The method of claim 10, wherein said immobilizing step is accomplished via a formaldehyde-based condensation reaction.

15. The method of claim 1, wherein if said target molecule is a protein, glycoprotein, or other water soluble macromolecule, then said exposing step is accomplished in solution.

16. The method of claim 15, wherein said first separating step is accomplished via one of size-exclusion chromatography, molecular weight cut off spin columns, dialysis, gel electrophoresis, thin layer chromatography (TLC), or differential centrifugation using density gradient materials.

17. The method of claim 7, wherein said third separating step is accomplished via ion pair reverse-phase high performance liquid chromatography, ion-exchange chromatography, thin layer chromatography, capillary electrophoresis, or similar techniques.

18. The method of claim 5, wherein said determining step comprises:
   digesting, in a first digesting step, the sequences and structures of said best FRET-aptamer using snake venom phosphodiesterase exonuclease on the 3' end of said unbound FRET-aptamer to generate oligonucleotide fragments;
   digesting, in a second digesting step, the sequences and structures of said unbound FRET-aptamer using calf spleen phosphodiesterase on the 5' end of said unbound FRET-aptamer to generate oligonucleotide fragments;
   performing mass spectral analysis of said oligonucleotide fragments; and
   determining the placement of said F and said Q in said best FRET-aptamer.

19. The method of claim 5, further comprising:
   lyophilization of said intrachain FRET-aptamers; and
   reconstitution of said intrachain FRET-aptamers.

20. A method of generating single-chain fluorescence resonance energy transfer ("FRET")-aptamers that contain both fluorophores and quenchers in the same single-stranded oligonucleotides, comprising:
   incorporating fluorophores and quenchers into an aptamer population using PCR wherein at least one of said fluorophores and at least one of said quenchers are incorporated into some of said oligonucleotides at random locations in the interior of said oligonucleotides;

exposing said aptamer population to a population of target molecules; and separating, in a first separating step, those FRET-aptamers that have bound to a target molecule and which emitted detectable fluorescence prior to binding said target molecule but said detectable fluorescence is reduced significantly after binding said target molecule, from the remaining aptamer population.

21. The method of claim 20, further comprising selecting a best FRET-aptamer that exhibits the least fluorescence from said FRET-aptamers.

22. The method of claim 20, wherein said target molecules are proteins.

23. The method of claim 20, wherein said first separating step is accomplished via one of size-exclusion chromatography columns, spin columns, or gel electrophoresis.

24. The method of claim 21, further comprising determining the nucleotide sequence of said best FRET-aptamer.

25. The method of claim 21, further comprising separating, in a second separating step, said FRET-aptamers that have bound to a target molecule from said target molecule wherein said second separating step is accomplished via introduced heating or chemicals.

26. The method of claim 25, further comprising separating, in a third separating step, said FRET-aptamers based upon specific physical properties.

27. The method of claim 20, wherein said fluorophores are selected from the group consisting of sulfonated versions of coumarins, rhodamine, xanthene dyes like fluoresceins and cyanine dyes such as ALEXFLUOR™-NTPs, pyreneoxytrisulfonic acid such as CASCADE BLUE®-NTPs, fluorescent dyes such as CHROMATIDE®-NTPs, fluorescein-NTPs, rhodamine-NTPs, carboxyrhodamines such as RHODAMINE GREEN™-NTPs, tetramethylrhodamine-dNTPs, fluorinated versions of fluorescein such as OREGON GREEN®-NTPs, and sulforhodamines such as TEXAS RED®-NTPs.

28. The method of claim 20, wherein said quenchers are selected from the group consisting of dabcyl-NTPs, non-fluorescent aromatic heterocycles such as BLACK HOLE QUENCHER or BHQ™-NTPs, and diarylrhodamine or nitrobenzoxazole quencher dyes such as QSY™ dye-NTPs.

29. The method of claim 20, wherein if said target molecule is a small molecule, wherein a small molecule is defined as a molecule with a molecular weight of $\leq$1,000 Daltons, then said exposing step is accomplished by immobilizing said small target molecule.

30. The method of claim 29, wherein said immobilizing step is accomplished on a column, membrane, plastic or glass bead, magnetic bead, or other matrix.

31. The method of claim 30, further comprising eluting bound aptamers from said column, membrane, plastic or glass bead, magnetic bead, or other matrix by use of 0.2-3.0M sodium acetate at a pH of between 3 and 7.

32. The method of claim 30, further comprising eluting bound aptamers from said column, membrane, plastic or glass bead, magnetic bead, or other matrix by use of 0.2-3.0M sodium acetate at a pH of 5.2.

33. The method of claim 29, wherein said immobilizing step is accomplished via a formaldehyde-based condensation reaction.

34. The method of claim 20, wherein if said target molecule is a protein, glycoprotein, or other water soluble macromolecule, then said exposing step is accomplished in solution.

35. The method of claim 34, wherein said first separating step is accomplished via one of size-exclusion chromatography, molecular weight cut off spin columns, dialysis, gel electrophoresis, thin layer chromatography (TLC), or differential centrifugation using density gradient materials.

36. The method of claim 26, wherein said third separating step is accomplished via ion pair reverse-phase high performance liquid chromatography, ion-exchange chromatography, thin layer chromatography, capillary electrophoresis, or similar techniques.

37. The method of claim 24, wherein said determining step comprises:

digesting, in a first digesting step, the sequences and structures of said best FRET-aptamer using snake venom phosphodiesterase exonuclease on the 3' end of said unbound FRET-aptamer to generate oligonucleotide fragments;

digesting, in a second digesting step, the sequences and structures of said unbound FRET-aptamer using calf spleen phosphodiesterase on the 5' end of said unbound FRET-aptamer to generate oligonucleotide fragments;

performing mass spectral analysis of said oligonucleotide fragments; and determining the placement of said F and said Q in said best FRET-aptamer.

38. The method of claim 24, further comprising:

lyophilization of said intrachain FRET-aptamers; and reconstitution of said intrachain FRET-aptamers.

* * * * *